United States Patent
Sambasivam et al.

(10) Patent No.: US 6,573,385 B1
(45) Date of Patent: Jun. 3, 2003

(54) PROCESS FOR MANUFACTURING SIMVASTATIN AND NOVEL INTERMEDIATES THEREOF

(75) Inventors: Ganesh Sambasivam, Bangalore (IN); Madhavan Sridharan, Karnataka (IN); Poornaprajna Acharya, Karnataka (IN); Joy Mathew, Karnataka (IN)

(73) Assignee: Biocon India Limited, Bangalore District (IN)

( * ) Notice: Subject to any disclaimer, the term of this patent is extended or adjusted under 35 U.S.C. 154(b) by 6 days.

(21) Appl. No.: 10/194,126

(22) Filed: Jul. 12, 2002

Related U.S. Application Data

(63) Continuation-in-part of application No. 10/129,861, filed on Nov. 11, 1999.

(51) Int. Cl.[7] ............ C07D 207/04; C07D 211/06; C07C 231/04
(52) U.S. Cl. ............ 546/314; 548/540; 564/133
(58) Field of Search ............ 546/314; 548/540; 564/133

(56) References Cited

U.S. PATENT DOCUMENTS

| | | | |
|---|---|---|---|
| 4,820,850 A | 4/1989 | Verhoeven et al. | 549/292 |
| 5,223,415 A | 6/1993 | Conder et al. | 435/125 |
| 5,393,893 A | 2/1995 | Kubela et al. | 549/292 |
| 5,763,646 A | 6/1998 | Kumar et al. | 560/252 |
| 5,763,653 A | 6/1998 | Khanna et al. | 560/252 |
| 5,917,058 A | 6/1999 | Kumar et al. | 549/292 |
| 5,939,564 A | 8/1999 | Kumar et al. | 549/292 |
| 6,252,091 B1 | 6/2001 | Zupancic et al. | 549/292 |
| 6,271,398 B1 | 8/2001 | Van Dalen et al. | 549/292 |
| 6,294,680 B1 | 9/2001 | Vries et al. | 549/373 |
| 6,307,066 B1 | 10/2001 | Murthy et al. | 549/292 |
| 6,331,641 B1 | 12/2001 | Taoka et al. | 549/292 |

FOREIGN PATENT DOCUMENTS

| | | |
|---|---|---|
| EP | 0 864 560 | 9/1998 |
| EP | 0 864 569 | 9/1998 |
| EP | 0 940 395 | 9/1999 |
| EP | 0 955 297 | 11/1999 |
| WO | WO 98/32751 | 7/1998 |
| WO | WO 99/11258 | 3/1999 |

*Primary Examiner*—Taofiq A. Solola
(74) *Attorney, Agent, or Firm*—Sam Pasternak; Choate, Hall & Stewart

(57) ABSTRACT

The present invention provides intermediates of formula IIb and IIc useful for the preparation of Simvastatin:

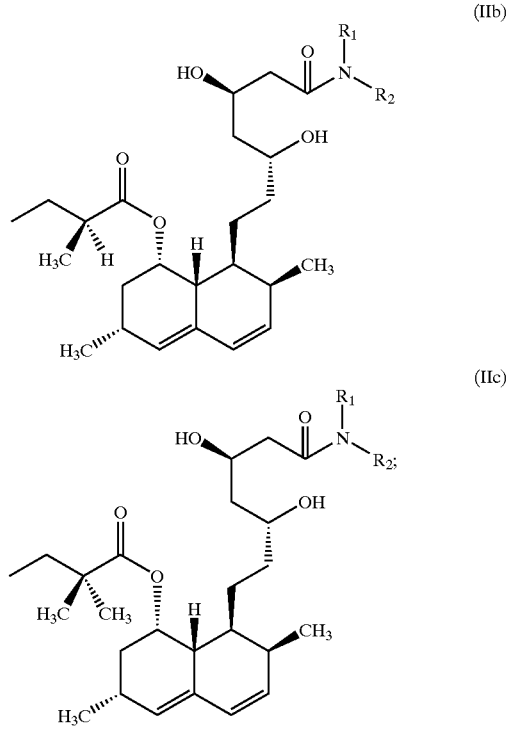

wherein $R_1$ and $R_2$ are each independently an alkyl, heteroalkyl, aryl or heteroaryl moiety, or $R_1$ and $R_2$, taken together, form a heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing heterocyclic, aryl and heteroaryl moieties may be substituted or unsubstituted.

8 Claims, No Drawings

PROCESS FOR MANUFACTURING SIMVASTATIN AND NOVEL INTERMEDIATES THEREOF

The present application is a Continuation-in-part of co-pending U.S. National Application Ser. No. 10/129,861, filed Nov. 11, 1999, under 35 U.S.C. §371, which is related to the subject matter in and claims benefit of published PCT application No. WO 01/34590 filed Nov. 11, 1999, each of which is incorporated herein by reference in its entirety.

BACKGROUND OF THE INVENTION

Certain hexahydronaphthalene derivatives are known as potent inhibitors of the enzyme HMG-CoA reductase, the rate-controlling enzyme in the biosynthetic pathway for formation of cholesterol in the human body. Well-known examples of these compounds are Mevastatin (U.S. Pat. No. 3,983,140), Lovastatin (U.S. Pat. No. 4,231,938), Pravastatin (U.S. Pat. No. 4,346,227) and Simvastatin (U.S. Pat. No. 4,444,784). All of these compounds are important pharmaceuticals and are widely used in hypercholesterolaemic treatments.

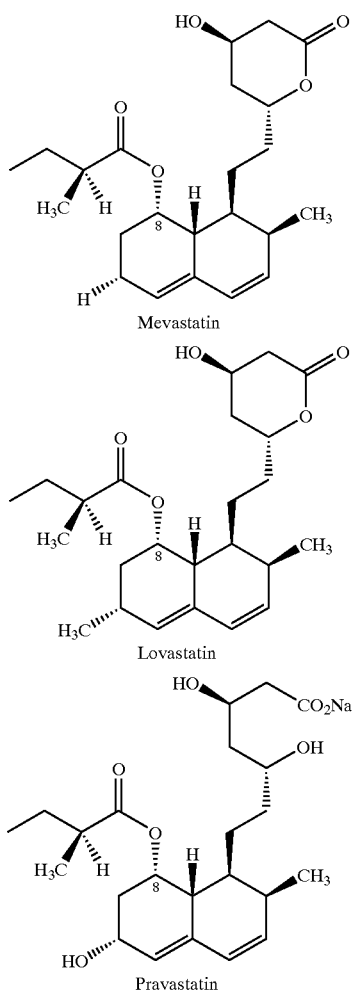

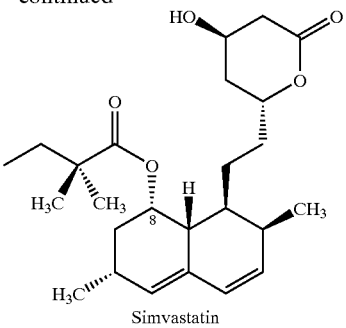

Simvastatin

Mevastatin (also known as Compactin), Lovastatin (i.e., Mevinolin) and Pravastatin are natural fermentation products which possess a 2-methylbutyrate side chain at C-8 of their hexahydronaphthalene ring system. It has been reported that compounds possessing a C-8 2,2-dimethylbutyrate side chain (e.g., Simvastatin) are better inhibitors of HMG-CoA reductase than their 2-methylbutyrate counterparts. For example, Simvastatin has been shown to be approximately twice as potent as Pravastatin and Lovastatin, while Mevastatin is the least powerful. Thus 2,2-dimethylbutyrate derivatives show greater promise for the treatment of, for example, artherosclerosis, hyperlipemia, familial hypercholesterolemia and similar disorders. However, these derivatives, including Simvastatin, are not naturally occurring and thus have to be produced synthetically. As a result, the introduction on the market of the more potent HMG-CoA reductase inhibitor Simvastatin has prompted the need for efficient, high yielding processes for manufacturing it.

Several processes for the preparation of Simvastatin from Lovastatin have been reported. For example, 2,2-dimethylbutyrate derivatives and processes for their preparation are disclosed in U.S. Pat. No. 4,444,784 and EPO patent No. 33538. However, the route described is both tedious and cumbersome and gives very poor overall yields. U.S. Pat. No. 4,444,784 discloses a synthetic route whereby an additional α-methyl group is introduced on the C-8 acyl side chain of Lovastatin or analogues thereof. This process involves indirect methylation of the C-8 side chain through several chemical steps: deesterification of the whole 2-methylbutyrate side chain, protection of the pyranone ring 4-hydroxy group with a tert-butyldimethylsilyl protective group, reesterification of the protected lactone with 2,2-dimethylbutyric acid, and deprotection of the pyranone ring hydroxy group. This procedure involves multiple chemical reactions with a low overall yield.

Another route, based on direct methylation of the C-8 acyl side chain of Lovastatin and its analogues, is disclosed in U.S. Pat. No. 4,582,915. Direct methylation of the 2-methylbutyrate side chain of Lovastatin is achieved, after conversion to an alkali metal salt, using a methylhalide in the presence of a strong base (metal alkylamide). The process suffers from poor conversion coupled with many side reactions which complicate both isolation and purification of the final product, Simvastatin.

The problems of low yields and poor quality of the final product have been addressed in a process disclosed in U.S. Pat. No. 4,820,850. This procedure comprises: (i) treatment of Lovastatin with butylamine to achieve ring-opening of the lactone, followed by the protection of the hydroxyl-groups therein with tert-butyldimethylsilyl chloride; (ii) treatment of the obtained protected intermediate with an alkalimetal amide followed by contact with alkylhalide to add an alkyl group to the 2-position of the butyrate side chain; (iii) removal of the silyl protective groups by an acid, preferably hydrofluoric acid; (iv) treatment with dilute base to hydrolyse the alkylamide; and (v) heating of the resulting carboxylate salt in a hydrocarbon solvent to reform the lactone. However, the process involves a large number of steps, hence affecting the overall yield. Furthermore, the process utilizes a highly expensive silylating agent to protect the hydroxyl groups thus rendering the route cost ineffective.

Another direct methylation process is described in U.S. Pat. No. 5,393,893, where a Lovastatin-$C_3$–$C_7$-alkyl amide, cycloalkylamide or aralkylamide is prepared. The hydroxyl-groups are then protected with a phenylboronic acid and the resulting intermediate is further reacted with an alkylhalide in the presence of a base to introduce the alkyl moiety on the C-8 butyrate side chain. Similarly as in the above-referenced patent, the subsequent steps leading to Simvastatin involve the removal of the protective groups, hydrolysis of the alkylamide and relactonization to from Simvastatin.

The above two synthetic routes, which involve the step of direct methylation, differ from each other in the nature of the OH-protective group used in forming the reaction intermediates. These protected intermediates are generally characterized by a silicon- or boron-containing protecting group. These processes all suffer from severe disadvantages such as excessive steps including those involved with the insertion and removal of protecting groups, and the relative lack of stability of the protected intermediates under the reaction conditions utilized in the synthetic sequence, in particular the strongly alkaline conditions used in the methylation step. As a result, undesirable amounts of by-products are formed during the synthesis, thereby requiring additional isolation and purification steps before a product of desired pharmaceutical quality can be obtained, and adversely affecting the cost and overall yield of the synthetic route. Furthermore, the protecting agents used are economically undesirable.

The problems associated with the cumbersome hydroxyl protection/deprotection strategy have been addressed in a process disclosed in U.S. Pat. Nos. 5,763,653 and 5,763,646. The process involves the synthesis of Simvastatin using Lovastatin or mevinolinic acid in salt form as the starting material. U.S. Pat. No. 5,763,653 describes a method for preparing Simvastatin from a Lovastatin amide intermediate prepared by treating Lovastatin or the salt form of mevinolinic acid with a primary amine such as cyclopropyl or butyl amine, without requiring the afore-mentioned hydroxyl protection/deprotection sequence. However, the use of a primary amine to effect the pyranone ring opening results in the formation of a primary Lovastatin amide intermediate which may in turn undergo undesired side reactions due to the presence of its amide hydrogen atom. For example, the amide hydrogen atom can react with the lithium amide base used in the α-methylation step, thereby necessitating a higher equivalent of the lithium amide base. Furthermore, undesired side reactions may occur with the methylating agent (e.g., methyl iodide), thereby lowering the overall yield.

Thus there remains a need for efficient and high-yielding processes for the preparation of Simvastatin and 2-alkyl-2-methylbutyrate analogues thereof.

SUMMARY OF THE INVENTION

The present invention discloses a new process for the preparation of compounds of formula I (e.g, 2-alkyl-2-methylbutyryloxy derivatives of Lovastatin, Mevastatin and related compounds).

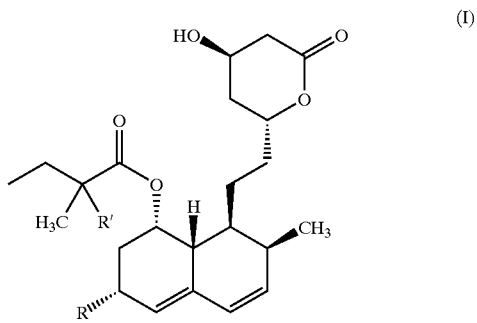

wherein R is hydrogen, hydroxyl or substituted or unsubstituted lower alkyl; and R' is substituted or unsubstituted lower alkyl.

In a preferred embodiment, the present invention provides a new process for he preparation of Simvastatin of formula II.

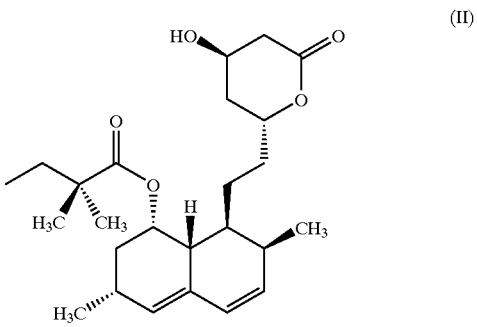

The method does not require the protection-deprotection sequence of the hydroxy groups generated from the lactone ring opening and thus does not necessitate the use of rather expensive silyl or other protecting agents. In addition, the method addresses the problems associated with primary statin amides as intermediates, particularly side-reactions (and thus lower yields) due to the primary amide hydrogen atom. Accordingly, the invention provides a highly effective method for the synthesis of Simvastatin and 2-alkyl-2-methylbutyrate Lovastatin and Mevastatin analogues by increasing the overall yield and purity of the final product, and by minimizing the cost of production of Simvastatin and analogues by utilizing inexpensive raw materials and a cost effective synthetic route.

In one aspect, the invention encompasses a method for preparing 2-alkyl-2-methylbutyryloxy derivatives of formula I, through a novel amide-protected intermediate generated from reaction of a lactone starting material with a secondary amine.

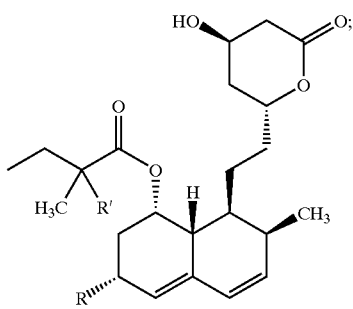

(I)

wherein R is H, OH or substituted or unsubstituted lower alkyl; and R' is substituted or unsubstituted lower alkyl.

In one embodiment, the method comprises steps of:

(i) reacting a compound of formula Ia:

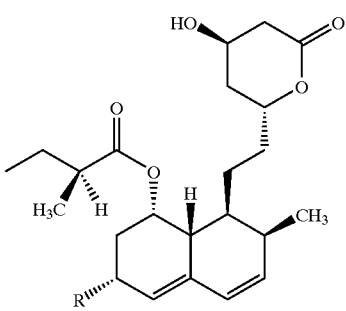

(Ia)

wherein R is H, OH or substituted or unsubstituted lower alkyl; with a secondary amine under suitable conditions to form the corresponding amide intermediate of formula Ib:

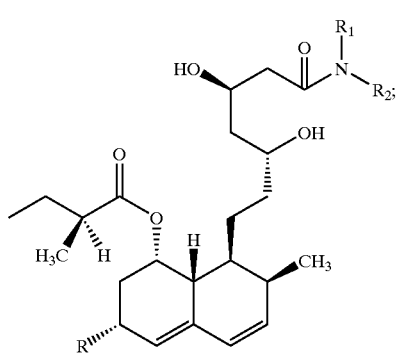

(Ib)

wherein R is as defined above; and $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted;

(ii) alkylating the C-8 butyrate side chain of the amide intermediate (Ib) under suitable conditions to form the corresponding 2-alkyl-2-methyl butyrate intermediate of formula Ic:

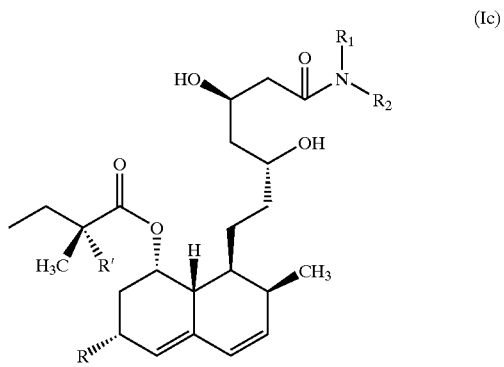

(Ic)

wherein R, $R_1$ and $R_2$ are as defined above; and R' is substituted or unsubstituted lower alkyl;

(iii) hydrolyzing the 2-alkyl-2-methyl butyrate intermediate to the corresponding free carboxylic acid; and (iv) effecting lactonization of the carboxylic acid intermediate thereby forming the desired 2-alkyl-2-methylbutyryloxy derivative of formula I.

In one embodiment, the alkylating step comprises reacting the Lovastatin amide with a non-nucleophilic base in an aprotic solvent, followed by treatment with a suitable alkylating agent. In preferred embodiments, the non-nucleophilic base is an alkali metal alkylamide. In certain preferred embodiments, the alkylating agent is an alkyl halide.

In another embodiment, the step of effecting lactonization of the carboxylic acid intermediate comprises converting the free carboxylic acid to the corresponding ammonium salt and cyclizing the ammonium salt under suitable conditions to obtain the desired 2-alkyl-2-methylbutyryloxy derivative of formula I.

In another aspect, the invention encompasses a method for preparing Simvastatin of formula II, through a novel amide-protected intermediate generated from reaction of Lovastatin with a secondary amine.

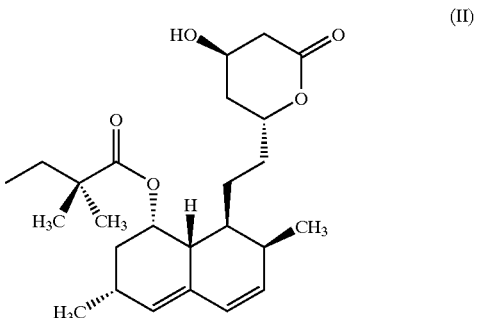

(II)

In one embodiment, the method comprises steps of:
(i) reacting Lovastatin of formula IIa:

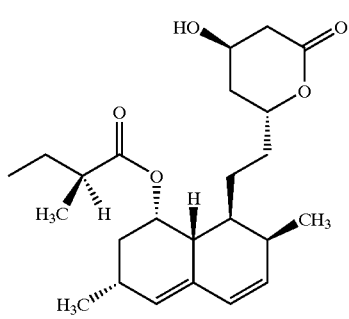

with a secondary amine under suitable conditions to form the corresponding amide intermediate of formula IIb:

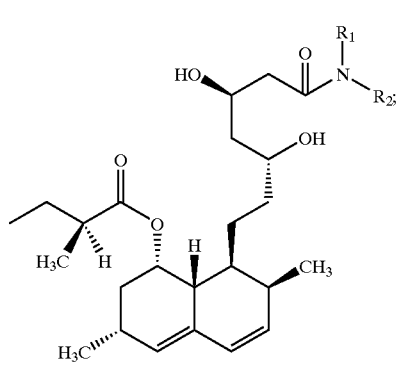

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted;

(ii) methylating the C-8 butyrate side chain of the amide intermediate (IIb) under suitable conditions to form the corresponding 2,2-dimethyl butyrate intermediate of formula IIc:

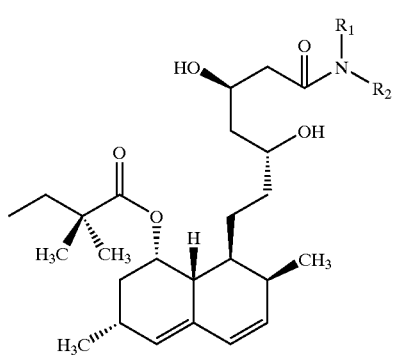

wherein $R_1$ and $R_2$ are as defined above;
(iii) hydrolyzing the 2,2-dimethyl butyrate intermediate to the corresponding free carboxylic acid; and (iv) effecting lactonization of the carboxylic acid intermediate thereby forming the desired Simvastatin of formula II.

In one embodiment, the methylating step comprises reacting the Lovastatin amide with a non-nucleophilic base in an aprotic solvent, followed by treatment with a suitable methylating agent. In preferred embodiments, the non-nucleophilic base is an alkali metal alkylamide. In certain preferred embodiments, the methylating agent is a methyl halide.

In another embodiment, the step of effecting lactonization of the carboxylic acid intermediate comprises converting the free carboxylic acid to the corresponding ammonium salt, and subsequently cyclizing the ammonium salt under suitable conditions to obtain the desired Simvastatin of formula II.

In yet another aspect, the invention provides novel intermediates useful for the preparation of 2-alkyl-2-methylbutyryloxy Lovastatin derivatives and analogues thereof.

In one embodiment, a novel intermediate of formula Ib is provided:

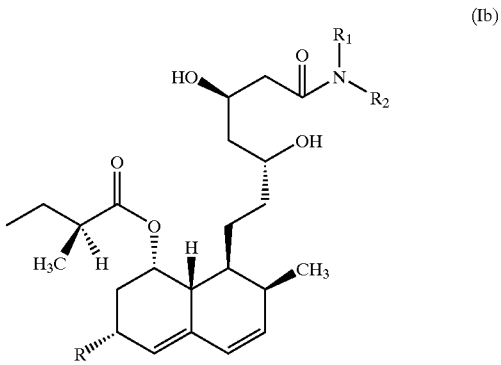

wherein R is hydrogen, hydroxyl or substituted or unsubstituted lower alkyl; and $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the novel intermediate has the following structure:

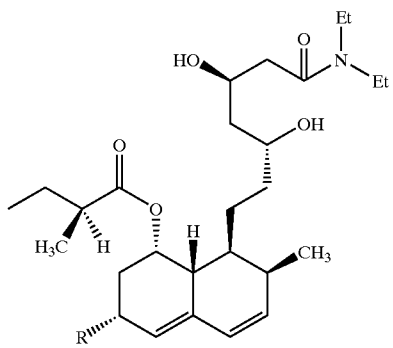

wherein R is as defined above.

In another embodiment, $R_1$ and $R_2$, taken together, form a 5–6 membered heterocyclic ring and the novel intermediate has the following structure:

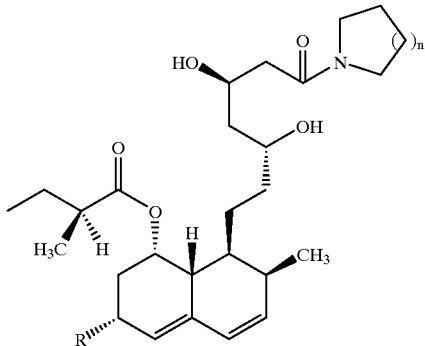

wherein n is 1 or 2 and R is as defined above.

In yet another embodiment, a novel intermediate of formula Ic is provided:

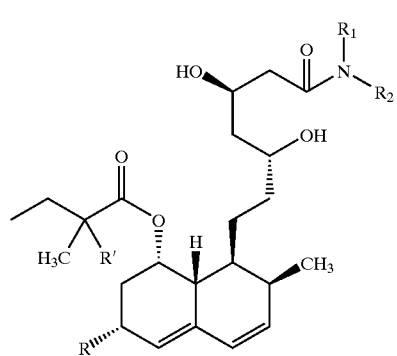

(Ic)

wherein R is hydrogen, hydroxyl or substituted or unsubstituted lower alkyl; R' is substituted or unsubstituted lower alkyl; and $R_1$ and $R_2$ are each independently an alkyl, heteroalkyl, aryl or heteroaryl moiety, or $R_1$ and $R_2$, taken together, form a saturated ro unsaturated heterocyclic moiety containing 5–8 atoms; wherein each of the foregoing alkyl and heteroalkyl moieties maybe linear or branched, substituted or unsubstituted, cyclic or acyclic or saturated or unsaturated, and each of the foregoing aryl and heteroaryl moieties may be substituted or unsubstituted.

In a further embodiment, $R_1$ and $R_2$, are each ethyl and the novel intermediate has the following structure:

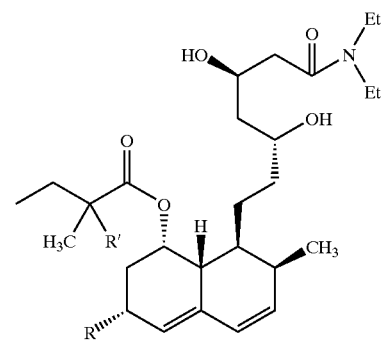

wherein R and R' are as defined above.

In another embodiment, $R_1$ and $R_2$, taken together, form a 5–6 membered heterocyclic ring and the novel intermediate has the following structure:

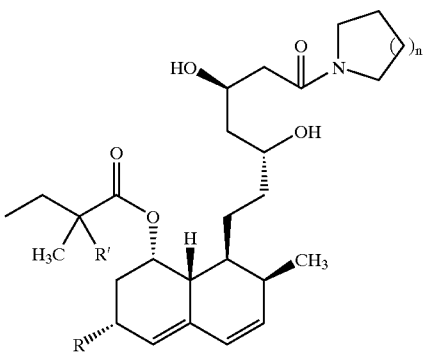

wherein n is 1 or 2; and R and R' are as defined above.

In a further aspect, the invention provides novel intermediates useful for the preparation of Simvastatin.

In one embodiment, a novel intermediate of formula IIb is provided:

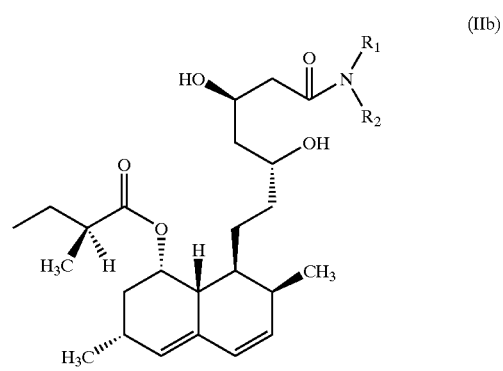

(IIb)

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the novel intermediate has the following structure:

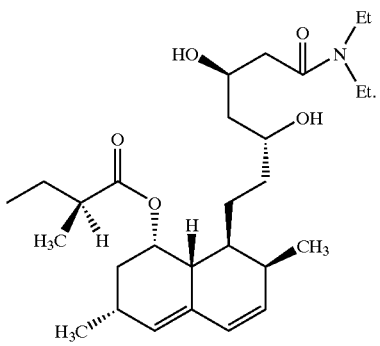

In another embodiment, $R_1$ and $R_2$, taken together, form a 5–6 membered heterocyclic ring and the novel intermediate has the following structure:

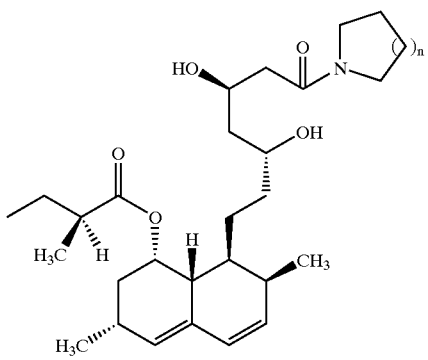

wherein n is 1 or 2.

In yet another embodiment, a novel intermediate of formula IIc is provided:

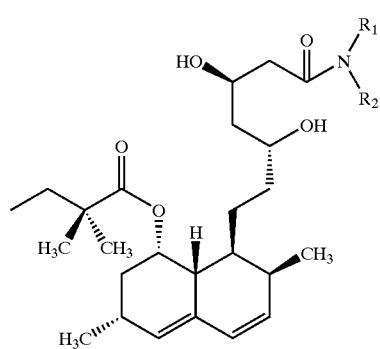
(IIc)

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In a further embodiment, $R_1$ and $R_2$ are each ethyl and the novel intermediate has the following structure:

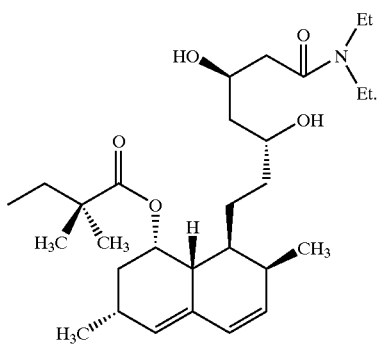

In another embodiment, $R_1$ and $R_2$, taken together, form a 5–6 membered heterocyclic ring and the novel intermediate has the following structure:

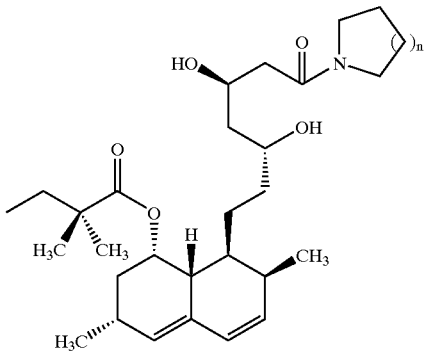

wherein n is 1 or 2.

Definitions

"Alkyl": the term alkyl as used herein refers to saturated, straight- or branched-chain hydrocarbon radicals derived from a hydrocarbon moiety containing between one and twenty carbon atoms by removal of a single hydrogen atom. Examples of alkyl radicals include, but are not limited to, methyl, ethyl, propyl, isopropyl, n-butyl, tert-butyl, n-pentyl, neopentyl, n-hexyl, n-heptyl, n-octyl, n-decyl, n-undecyl, and dodecyl, each of which may be substituted or unsubstituted.

In general, the term "substituted" refers to the replacement of hydrogen radicals i n a given structure with the radical of a specified substituent. When more than one position in any given structure may be substituted with more than one substituent selected from a specified group, the substituent may be either the same or different at every position. As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Heteroatoms such as nitrogen may have hydrogen substituents and/or any permissible substituents of organic compounds described herein which satisfy the valencies of the heteroatoms. Examples of substituents include, but are not limited to aliphatic; heteroaliphatic; aryl; heteroaryl; alkylaryl; alkylheteroaryl; alkoxy; aryloxy; heteroalkoxy; heteroaryloxy; alkylthio; arylthio; heteroalkylthio; heteroarylthio; F; Cl; Br; I; —OH; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —NR$_x$(CO)R$_x$ wherein each occurrence of R$_x$ independently includes, but is not limited to, aliphatic, heteroaliphatic, aryl, heteroaryl, alkylaryl, or alkylheteroaryl, wherein any of the aliphatic, heteroaliphatic, alkylaryl, or alkylheteroaryl substituents described above and herein may be substituted or unsubstituted, branched or unbranched, cyclic or acyclic, and wherein any of the aryl or heteroaryl substituents described above and herein may be substituted or unsubstituted.

In general, the term "aliphatic", as used herein, includes both saturated and unsaturated, straight chain (i.e., unbranched), branched, cyclic, or polycyclic aliphatic hydrocarbons, which are optionally substituted with one or more functional groups. As will be appreciated by one of ordinary skill in the art, "aliphatic" is intended herein to include, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. Illustrative aliphatic groups thus include, but are not limited to, for example, methyl, ethyl, n-propyl, isopropyl, cyclopropyl, —CH$_2$-cyclopropyl, allyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl-n, hexyl, sec-hexyl, cyclohexyl, —CH$_2$-cyclohexyl moieties and the like, which again, may bear one or more substituents. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

In general the term "heteroaliphatic", as used herein, refers to aliphatic moieties which contain one or more oxygen sulfur, nitrogen, phosphorus or silicon atoms, e.g., in place of carbon atoms. Heteroaliphatic moieties may be branched, unbranched, cyclic or acyclic and include saturated and unsaturated heterocycles such as morpholino, pyrrolidinyl, etc. The term heteroaliphatic also refers to moieties that are substituted by independent replacement of one or more of the hydrogen atoms thereon with one or more moieties. Substituents include, but are not limited to, any of the previously mentioned substitutents, i.e., the substituents recited for alkyl moieties resulting in the formation of a stable compound.

"Heteroalkyl": the term heteroalkyl as used herein refers to alkyl moieties which contain one or more oxygen sulfur, nitrogen, phosphorus or silicon atoms, e.g., in place of carbon atoms. Heteroalkyl moieties may be branched, unbranched, cyclic or acyclic and include saturated and unsaturated heterocycles such as morpholino, pyrrolidinyl, etc. The term heteroalkyl also refers to moieties that are substituted by independent replacement of one or more of the hydrogen atoms thereon with one or more moieties. Examples of heteroalkyl radicals include, but are not limited to, pyrrolidinyl, piperidinyl, piperazinyl, morpholinyl, tetrahydropyranyl, tetrahydrofuranyl, tetrahydrothiopyranyl, and tetrahydrothiophenyl, each of which may be substituted or unsubstituted. Substituents include, but are not limited to, any of the previously mentioned substitutents, i.e., the substituents recited for alkyl moieties resulting in the formation of a stable compound.

"Aryl" and "Heteroaryl": the terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include, but are not limited to, any of the previously mentioned substitutents, i.e., the substituents recited for alkyl moieties resulting in the formation of a stable compound. The term aryl may refer to a mono- or bicyclic carbocyclic ring system having one or two aromatic rings including, but not limited to, phenyl, naphthyl, tetrahydronaphthyl, indanyl, indenyl and the like. The term heteroaryl, as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, such as, for example, pyridyl, pyrazinyl, pyrimidinyl, pyrrolyl, pyrazolyl, imidazolyl, thiazolyl, oxazolyl, isooxazolyl, thiadiazolyl, oxadiazolyl, thiophenyl, furanyl, quinolinyl, isoquinolinyl, and the like.

"Amine": the term amine, as used herein, does not substantially differ from the common meaning of this term in the art, and refers to a molecule having one, two, or three moieties independently selected from the group consisting of alkyl, heteroalkyl, aryl or heteroaryl groups, as previously defined, attached to a nitrogen atom. Each of the foregoing alkyl, heteroalkyl, aryl or heteroaryl groups may be substituted or unsubstituted. Substituents include, but are not limited to, any of the previously mentioned substitutents, i.e., the substituents recited for alkyl moieties resulting in the formation of a stable compound. The term primary amine refers to a molecule having the structure R'NH$_2$ wherein R' is an alkyl group, as previously defined; the term secondary amine refers to a molecule having the structure R'R"NH, wherein R' and R" are each independently selected from the group consisting of alkyl groups; and the term tertiary amine refers to a molecule having the structure NR'R"R''', wherein R', R", and R''' are each independently selected from the group consisting of alkyl groups. Additionally, R', R", and/or R''' taken together may optionally be —(CH$_2$)$_k$— where k is an integer from 2 to 6. Examples of primary amines include, but are not limited to, methylamine, ethylamine, n-propylamine, i-propylamine and n-butylamine. Examples of secondary amines include, but are not limited to, dimethylamine, diethylamine, methylethylamine, di-idopropylamine, pyrrolidine and piperidine. Examples of tertiary amines include, but are not limited to, trimethylamine, triehtylamine and N-methylpiepridine.

"Amide": The term Amide, as used herein, does not substantially differ from the common meaning of this term in the art, and refers to a moiety of structure —C(O)NR$_1$R$_2$, wherein R$_1$ and R$_2$ are independently hydrogen or a substituted or unsubstituted, cyclic or acyclic, linear or branched, saturated or unsaturated aliphatic, heteroaliphatic, aryl or heteroaryl moiety.

"Carboxylic acid ": The term carboxylic acid as used herein refers to a group of formula —CO$_2$H.

"Halo, halide and halogen": The terms halo, halide and halogen as used herein refer to an atom selected from fluorine, chlorine, bromine, and iodine.

"Lithium amide base": The term lithium amide base, as used herein, refers to a chemical entity having the structure Li$^{+-}$NR$_1$R$_2$; wherein R$_1$ and R$_2$ are each independently hydrogen, —CR$_x$R$_y$R$_z$ or —SiR$_x$R$_y$R$_z$; or R$_1$ and R$_2$, taken together form a saturated or unsaturated heterocyclic moiety containing 5–8 atoms; wherein R$_x$, R$_y$ and R$_z$ are each independently hydrogen, alkyl, heteroalkyl, aryl or heteroaryl; whereby each of the foregoing alkyl and heteroalkyl moiety may be substituted or unsubstituted, linear or branched, cyclic or acyclic or saturated or unsaturated; and each of the foregoing aryl, heteroaryl and heterocyclic moiety may be substituted or unsubstituted.

DETAILED DESCRIPTION OF CERTAIN PREFERRED EMBODIMENTS OF THE INVENTION

Certain preferred embodiments of the invention will now be more particularly described and pointed out in the following text. It will be understood that the particular embodiments of the invention are shown by way of illustration and not as limitations of the invention. Principle features of the invention may be employed in various embodiments without departing from the scope of the invention.

It is known that Lovastatin (in its lactone form) cannot be converted directly to Simvastatin by an enolate alkylation reaction because of concurrent alkylation at the lactone α-position (D. Askin, T. R. Verhoeven, H. Liu, and I. Shinkai J. Org. Chem. 1991, 56, 4929) due to the higher acidity (approximately 3 pKa units) of the lactone α-hydrogens compared with the C-8 side chain ester α-hydrogen (K. B. Wiberg, K. E. Laidig J. Am. Chem. Soc. 1988, 110, 1872). The present invention provides a method for preparing Simvastatin or formula II, as well as 2-alkyl-2-methylbutyrate Lovastatin derivatives of formula I or analogues thereof, by direct alkylation of the butyrate side chain of Lovastatin or analog thereof.

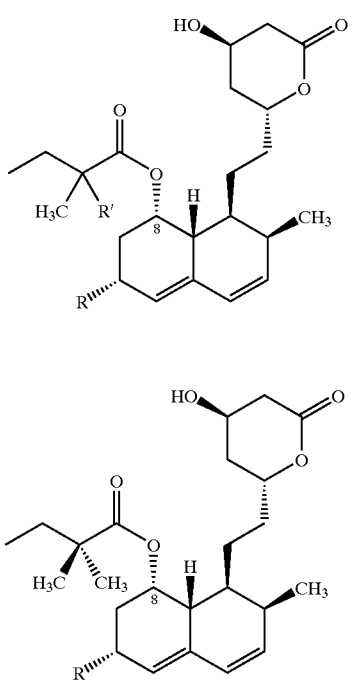

wherein R is hydrogen, hydroxyl or substituted or unsubstituted lower alkyl; and R' is substituted or unsubstituted lower alkyl.

As depicted in Scheme 1, the method involves ring opening of the statin-type starting material (Ia) with a secondary amide, resulting in an amide-protected intermediate (Ib) that is highly stable to alkaline alkylation conditions. In addition, conversion of the lactone starting material (Ia) to the corresponding acyclic amide intermediate (Ib) effectively results in a reversal of the acidic character of the "latent lactone" α-hydrogen atoms versus the butyrate side chain α-hydrogen atom.

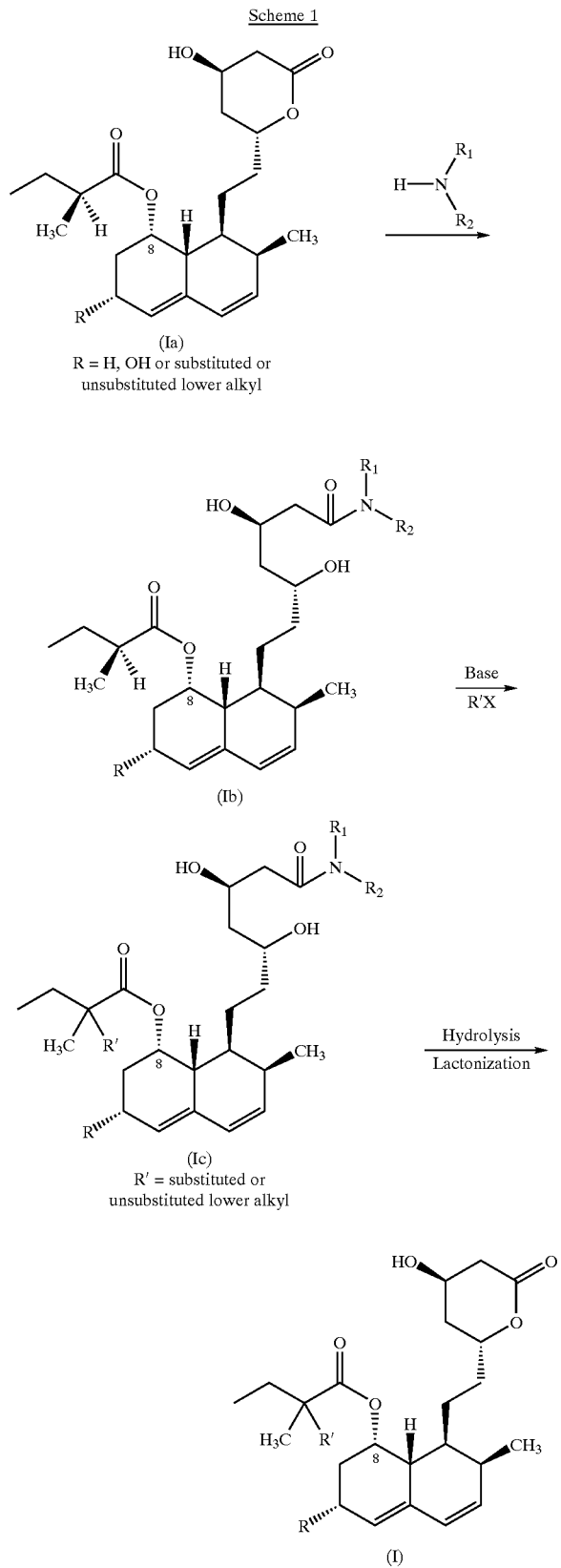

For the purpose of the invention, term "latent lactone" is taken to mean a protected lactone (e.g., amide-protected intermediate (Ib)), which, upon deprotection, yields the original lactone. The carbonyl α-hydrogen atom on the butyrate side chain is now more acidic than the amide α-hydrogens, and can therefore be selectively removed with a suitable base. The enolate species resulting from selective deprotonation of the butyrate chain α-hydrogen atom is then alkylated to produce a 2-alkyl-2-methylbutyryloxy intermediate (Ic). Upon hydrolysis of the amide moiety to the corresponding carboxylic acid and lactonization, the desired 2-alkyl-2-methylbutyryloxy product (I) is obtained.

In one embodiment, the method comprises steps of:

(i) reacting a compound of formula Ia:

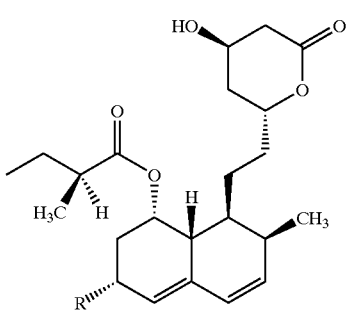

(Ia)

wherein R is H, OH or substituted or unsubstituted lower alkyl; with a secondary amine under suitable conditions to form the corresponding amide intermediate of formula Ib:

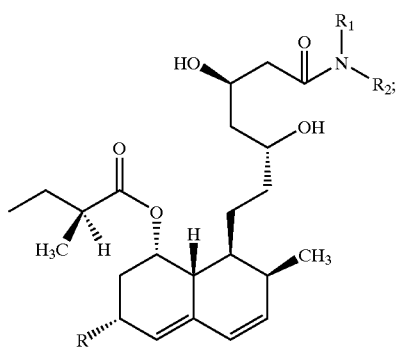

(Ib)

wherein R is as defined above; and $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted;

(ii) alkylating the C-8 butyrate side chain of the amide intermediate (Ib) under suitable conditions to form the corresponding 2-alkyl-2-methyl butyrate intermediate of formula Ic:

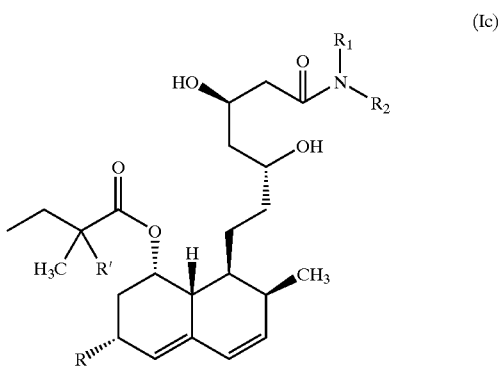

(Ic)

wherein R, $R_1$ and $R_2$ are as defined above; and R' is substituted or unsubstituted lower alkyl;

(iii) hydrolyzing the 2-alkyl-2-methyl butyrate intermediate to the corresponding free carboxylic acid; and (iv) effecting lactonization of the carboxylic acid intermediate thereby forming the desired 2-alkyl-2-methylbutyryloxy derivative of formula I:

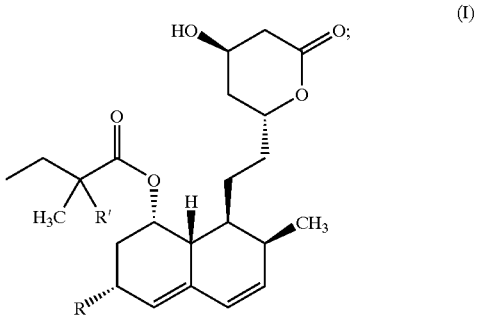

(I)

wherein R and R' are as defined above.

In another embodiment, the reaction between compound Ia and the secondary amine is carried out in an organic solvent. The solvent may be polar or non polar. Examples of suitable solvents include, but are not limited to, benzene and toluene, to name a few. Alternatively, the secondary amine may be used in excess and serve as the solvent for carrying out the amide protection reaction. Any secondary amine in liquid form under the conditions of the reaction may be used. Examples of suitable secondary amines include, but are not limited to, diethylamine, diisopropylamine, dibutylamine, pyrrolidine and piperidine, to name a few. In certain preferred embodiments, the secondary amine is diethylamine, and the amide intermediates $Ib_1$ and $Ic_1$ involved in the preparation of 2-alkyl-2-methylbutyrate compound (I) are those depicted in Scheme 2.

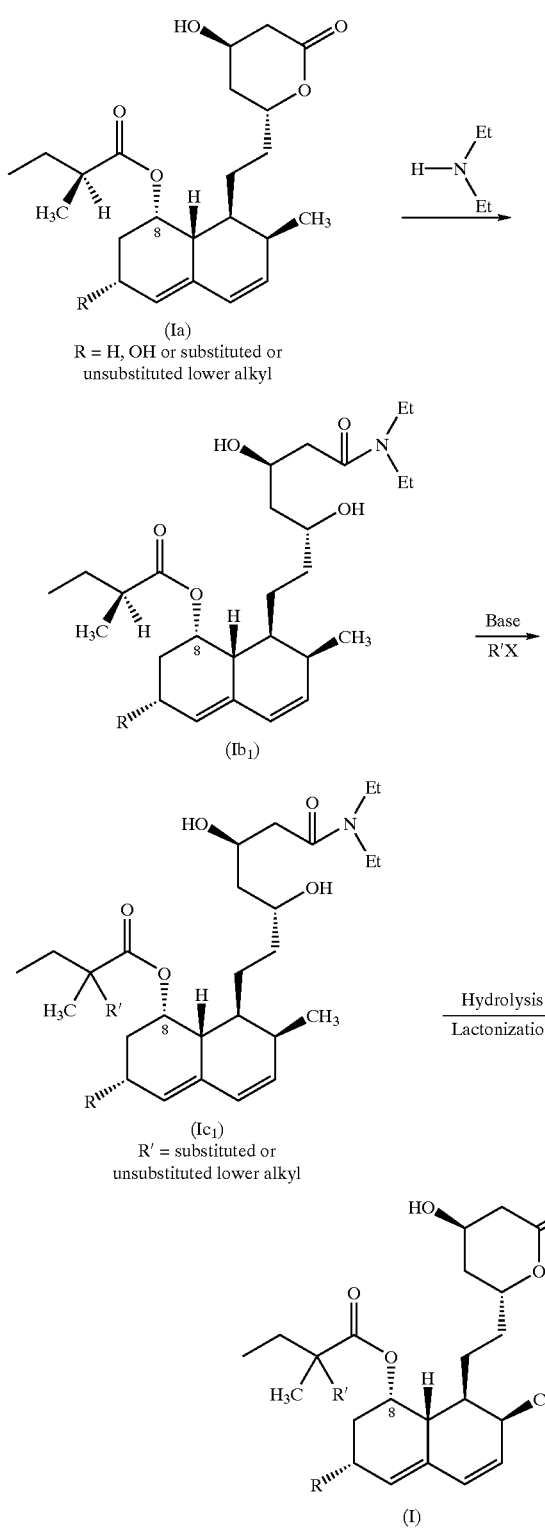

Scheme 2

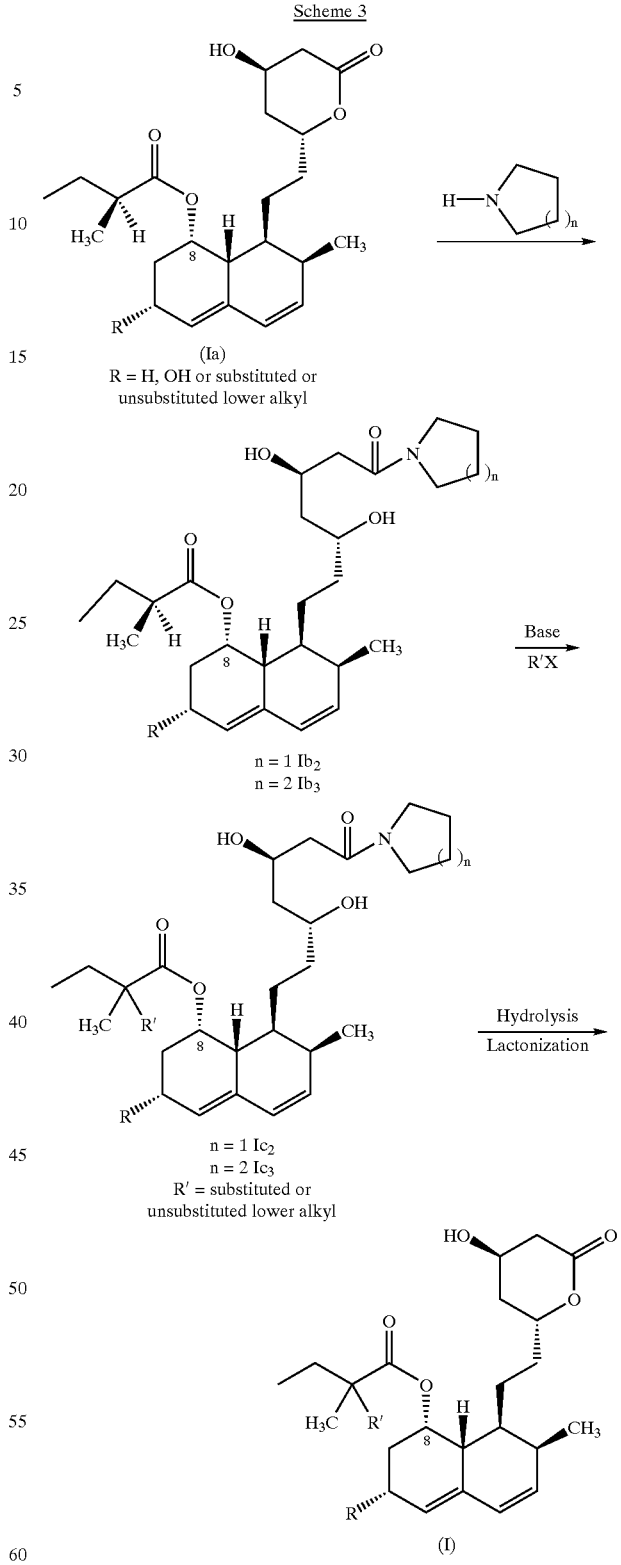

Scheme 3

In other preferred embodiments, the secondary amine is pyrrolidine or piperidine, and the amide intermediates $Ib_{2-3}$ and $Ic_{2-3}$ involved in the preparation of 2-alkyl-2-methylbutyrate compound (I) are those depicted in Scheme 3:

In yet another embodiment, the alkylating step comprises reacting the amide intermediate (Ib) with a base in an organic solvent, followed by treatment with a suitable alkylating agent. Preferably, the organic solvent is an aprotic solvent. Examples of suitable aprotic solvents include, but are not limited to, $Et_2O$, tetrahydrofuran (THF), hexane, 1,2-dimethoxyethane (DME), N,N-dimethylformamide (DMF), or combination thereof. Most preferably, the solvent is THF.

In certain preferred embodiments, the base is a strong non-nucleophilic base. Examples of bases suitable for practicing the invention include, but are not limited to, potassium hydride (KH), potassium tert-butoxide (tert-BuOK), sodium amide ($NaNH_2$) and lithium amide bases. In preferred embodiments, the base is a lithium amide base. Examples of lithium amide bases suitable to practice the invention include, but are not limited to, lithium diethylamide, lithium diisopropylamide (LDA), lithium pyrrolidinamide, lithium piperidinamide, lithium isopropylcyclohexylamide and lithium hexamethyl disilazide (LHMDS). Typically, a lithium amide base is prepared by reacting an amine with an organolithium reagent under suitable conditions. Examples of organolithium reagents suitable for practicing the invention include, but are not limited to, n-butyllithium, sec-butyllithium, tert-butyllithium and phenyllithium, to name a few.

In certain embodiments, the alkylating agent is a compound having the structure R'X, wherein R' is a substituted or unsubstituted lower alkyl moiety and X is a leaving group. Examples of alkylating agents suitable for practicing the invention include, but are not limited to, $R'N_2^+$, $R'OSO_2C_4F_9$, $R'OSO_2CF_3$, $R'OSO_2F$, R'OTs or R'Y; wherein Ts represents a tosyl moiety and Y represents a halide atom. In preferred embodiments, the alkylating agent is an alkyl halide. Preferably, but not necessarily, the alkyl halide is an alkyl iodide. Most preferably, the alkyl iodide is methyl iodide.

In a further embodiment, the step of effecting lactonization of the carboxylic acid intermediate comprises converting the free carboxylic acid to the corresponding ammonium salt, followed by cyclizing the ammonium salt under suitable conditions to obtain the desired 2-alkyl-2-methylbutyryloxy derivative of formula I. In a preferred embodiment, cyclization of the carboxyl ammonium salt intermediate is effected thermally.

In certain embodiments, the invention provides novel intermediates useful for the preparation of 2-alkyl-2-methylbutyryloxy Lovastatin derivatives and analogues thereof.

In one embodiment, a novel intermediate of formula Ib is provided:

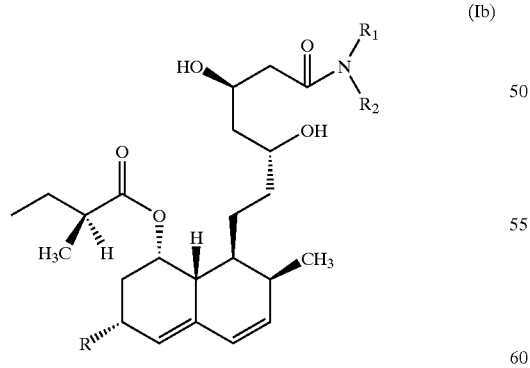

(Ib)

wherein R is hydrogen, hydroxyl or substituted or unsubstituted lower alkyl; and $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the intermediate has the structure $Ib_1$:

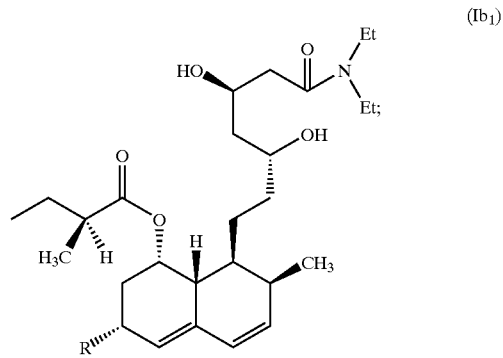

($Ib_1$)

wherein R is as defined above.

In another embodiment, $R_1$ and $R_2$, taken together, form a 5–6 membered heterocyclic ring and the novel intermediate has the following structure:

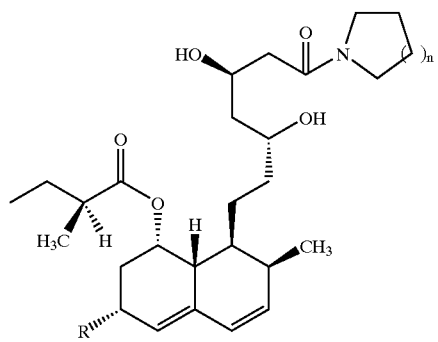

wherein n is 1 or 2 and R is as defined above.

In yet another embodiment, a novel intermediate of formula Ic is provided:

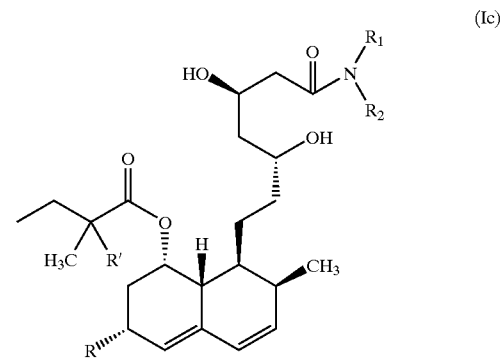

(Ic)

wherein R is hydrogen, hydroxyl or substituted or unsubstituted lower alkyl; R' is substituted or unsubstituted lower alkyl; and $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the intermediate has the structure $Ic_1$:

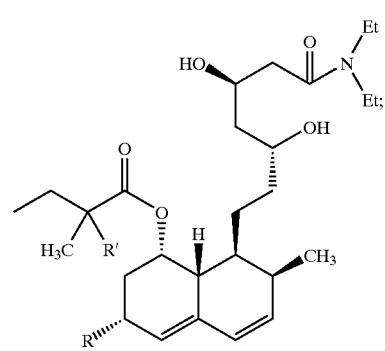

(Ic$_1$)

wherein R and R' are as defined above.

In a further embodiment, $R_1$ and $R_2$, taken together, form a 5–6 membered heterocyclic ring and the novel intermediate has the following structure:

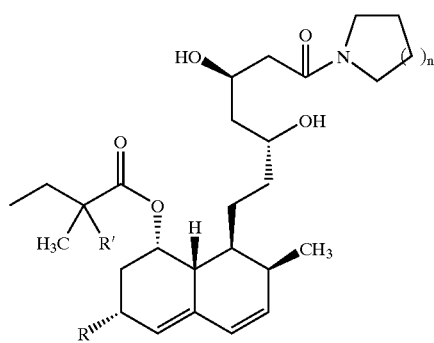

wherein n is 1 or 2; and R and R' are as defined above.

One of ordinary skill in the art will appreciate that the method may be applied to the preparation of Simvastatin (R and R' are each methyl). For example, as depicted in Scheme 4, ring opening of the Lovastatin starting material (IIa) with a secondary amide results in an amide-protected intermediate (IIb) that is highly stable to alkaline alkylation conditions. The carbonyl α-hydrogen atom on the butyrate side is selectively removed with a suitable base. The enolate species resulting from selective deprotonation of the butyrate chain α-hydrogen atom is then methylated to produce a 2,2-dimethylbutyryloxy intermediate (IIc). Upon hydrolysis of the amide moiety to the corresponding carboxylic acid, followed by lactonization, the desired Simvastatin of formula II is obtained.

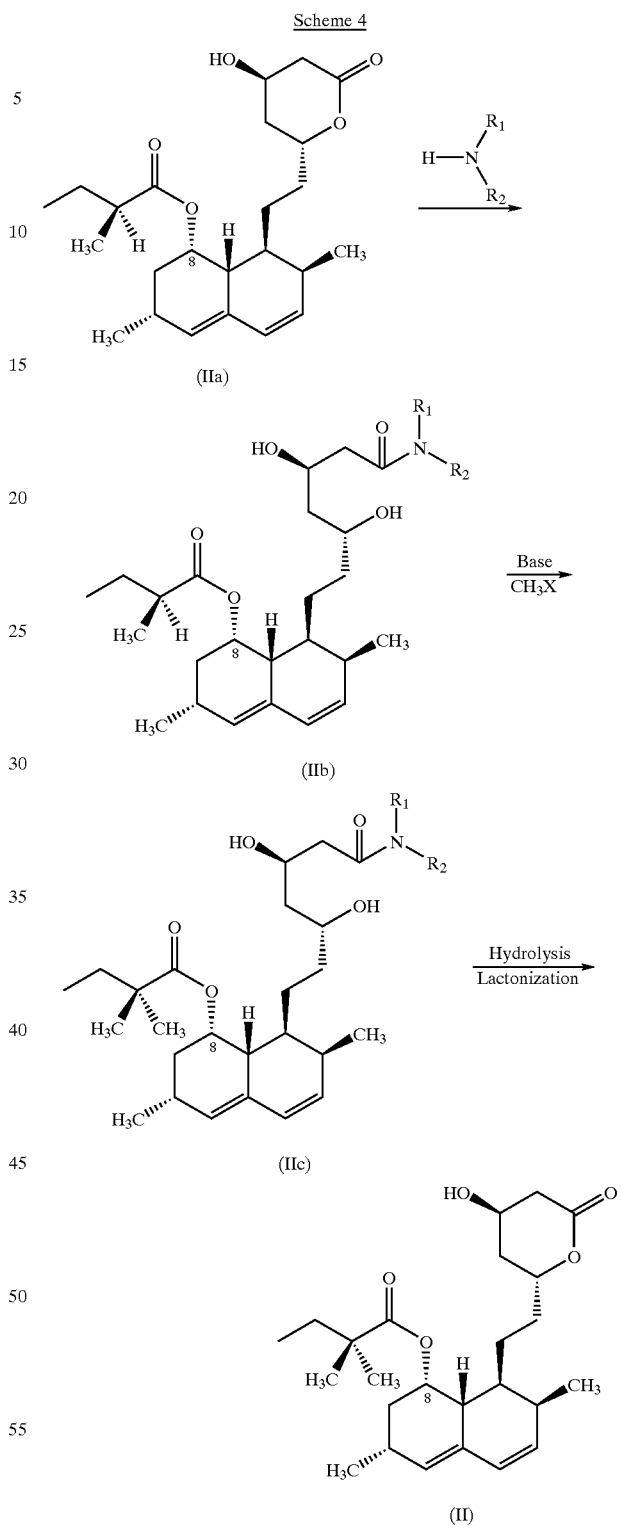

Scheme 4

R = H, OH or lower alkyl

In certain embodiments, the invention provides a method for preparing Simvastatin of formula II, through a novel amide-protected intermediate generated from reaction of Lovastatin with a secondary amine. In one embodiment, the method comprises steps of:

(i) reacting Lovastatin of formula IIa:

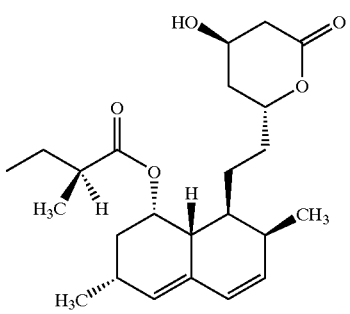

(IIa)

with a secondary amine under suitable conditions to form the corresponding amide intermediate of formula IIb:

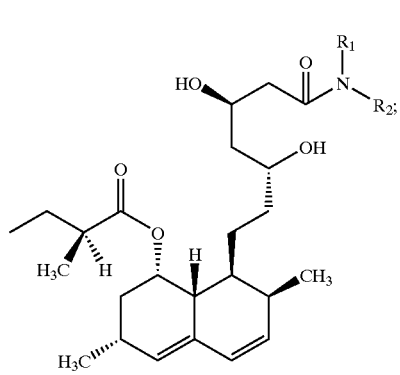

(IIb)

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted;

(ii) methylating the C-8 butyrate side chain of the amide intermediate (IIb) under suitable conditions to form the corresponding 2,2-dimethylbutyrate intermediate of formula IIc:

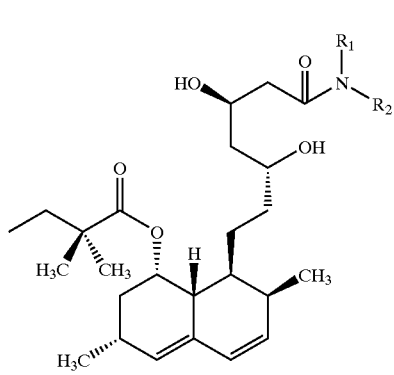

(IIc)

wherein $R_1$ and $R_2$ are as defined above;

(iii) hydrolyzing the 2,2-dimethylbutyrate intermediate to the corresponding free carboxylic acid; and (iv) effecting lactonization of the carboxylic acid intermediate thereby forming the desired Simvastatin of formula II.

In another embodiment, the reaction between compound IIa and the secondary amine is carried out in an organic solvent. The solvent may be polar or non polar. Examples of suitable solvents include, but are not limited to, benzene and toluene, to name a few. Alternatively the secondary amine may be used in large excess and serve as the solvent for carrying out the amide protection reaction. Any secondary amine in liquid form under the conditions of the reaction may be used. Examples of suitable secondary amines include, but are not limited to, diethylamine, diisopropylamine, dibutylamine, pyrrolidine and piperidine, to name a few. In certain preferred embodiments, the secondary amine is diethylamine, and the amide intermediates $IIb_1$ and $IIc_1$ involved in the preparation of Simvastat in II are those depicted in Scheme 5.

Scheme 5

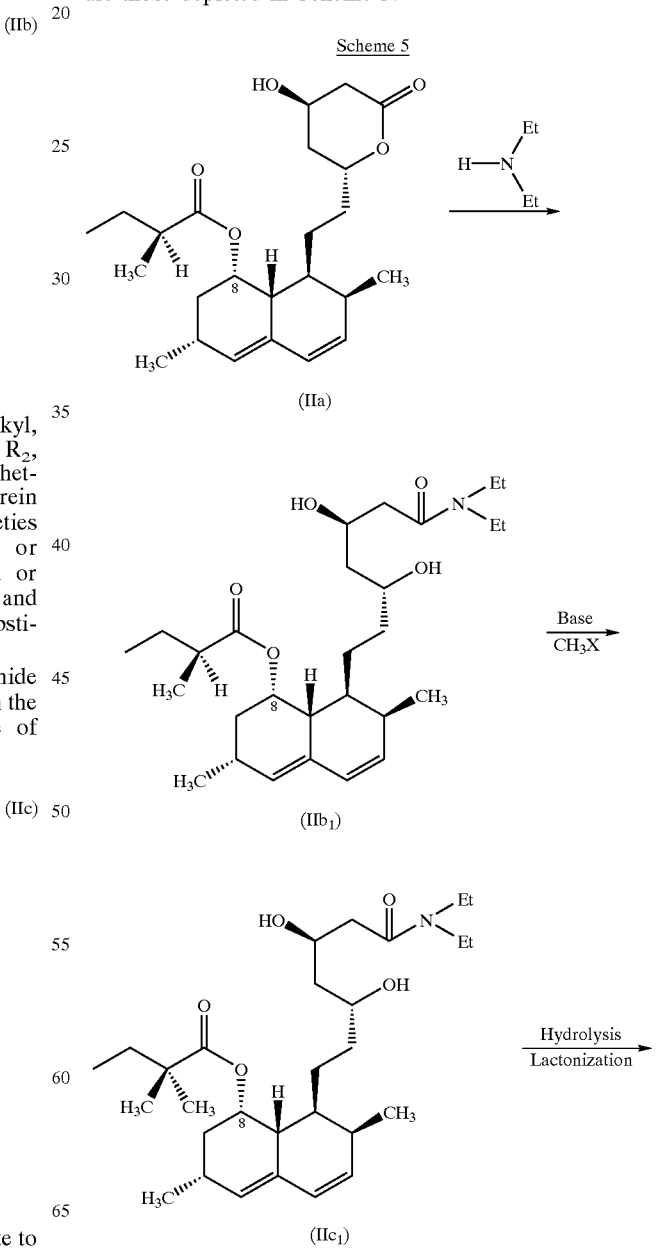

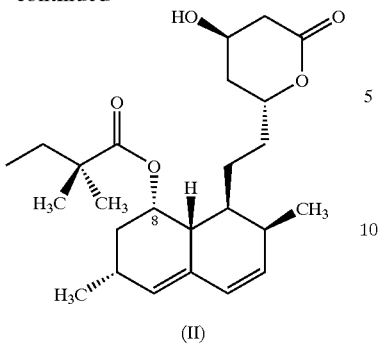

(II)

In other preferred embodiments, the secondary amine is pyrrolidine or piperidine, and the amide intermediates IIb$_{2-3}$ and Ic$_{2-3}$ involved in the preparation of Simvastatin II are those depicted in Scheme 6.

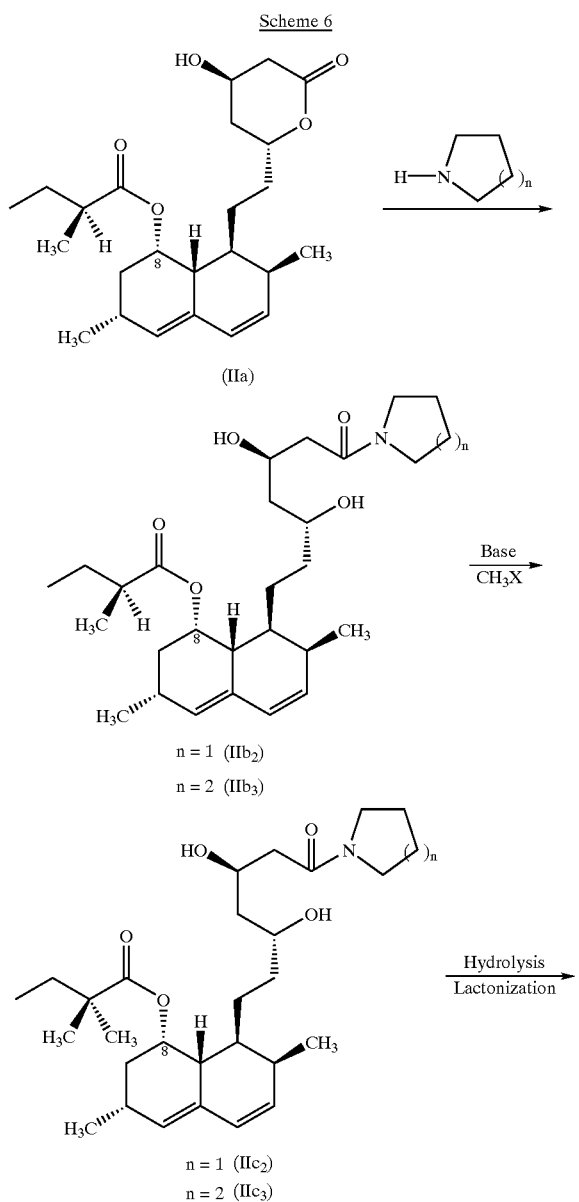

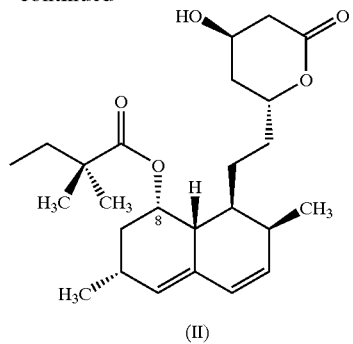

(II)

In yet another embodiment, the methylating step comprises reacting the amide intermediate (IIb) with a base in an organic solvent, followed by treatment with a suitable methylating agent. Preferably, the organic solvent is an aprotic solvent. Examples of suitable aprotic solvents include, but are not limited to, Et$_2$O, tetrahydrofuran (THF), hexane, 1,2-dimethoxyethane (DME), N,N-dimethylformamide (DMF), or combination thereof. Most preferably, the solvent is THF.

In certain preferred embodiments, the base is a strong non-nucleophilic base. Examples of bases suitable for practicing the invention include, but are not limited to, potassium hydride (KH), potassium tert-butoxide (tert-BuOK), sodium amide (NaNH$_2$) and lithium amide bases. In preferred embodiments, the base is a lithium amide base. Examples of lithium amide bases suitable to practice the invention include, but are not limited to, lithium diethylamide, lithium diisopropylamide (LDA), lithium pyrrolidinamide, lithium piperidinamide, lithium isopropylcyclohexylamide and lithium hexamethyl disilazide (LHMDS). Typically, a lithium amide base is prepared by reacting an amine with an organolithium reagent under suitable conditions. Examples of organolithium reagents suitable for practicing the invention include, but are not limited to, n-butyllithium, sec-butyllithium, tert-butyllithium and phenyllithium, to name a few. Most preferably the organolithium reagent is n-butyllithium.

In preferred embodiments, the lithium amide base is lithium pyrrolidide and is prepared by adding n-butyllithium to pyrrolidine in dry THF at a temperature ranging between −78° C. to −20° C. In more preferred embodiments, lithium pyrrolidide and is prepared by adding n-butyllithium to pyrrolidine in dry THF at a temperature ranging between −45° C. to −20° C.

In certain embodiments, the methylating agent is a compound having the structure CH$_3$X, wherein X is a leaving group. Examples of methylating agents suitable for practicing the invention include, but are not limited to, CH$_3$N$_2^+$, CH$_3$OSO$_2$C$_4$F$_9$, CH$_3$OSO$_2$CF$_3$, CH$_3$OSO$_2$F, CH$_3$OTs or CH$_3$Y; wherein Ts represents a tosyl moiety and Y represents a halide atom. In preferred embodiments, the methylating agent is a methyl halide. Most preferably, the methylating agent is methyl iodide.

In a preferred embodiment, methylation of Lovastatin amide intermediate IIb is effected by reacting IIb with a suitable lithium amide base at a temperature ranging between −78° C. to −20° C. Preferably, methylation is effected by reacting IIb with a suitable lithium amide base at a temperature ranging between −45° C. to −20° C. Most preferably, the temperature is about −30° C.

In a further embodiment, the step of effecting lactonization of the carboxylic acid intermediate comprises converting the free carboxylic acid to the corresponding ammonium salt, followed by cyclizing the ammonium salt under suitable conditions to obtain the desired Simvastatin of formula II. In a preferred embodiment, cyclization of the carboxyl ammonium salt intermediate is effected thermally.

In certain embodiments, the invention provides novel intermediates useful for the preparation of Simvastatin.

In one embodiment, a novel intermediate of formula IIb is provided:

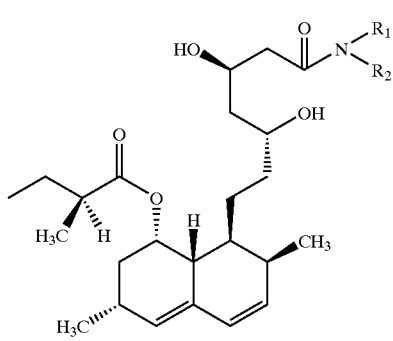

(IIb)

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the novel intermediate has the structure $IIb_1$:

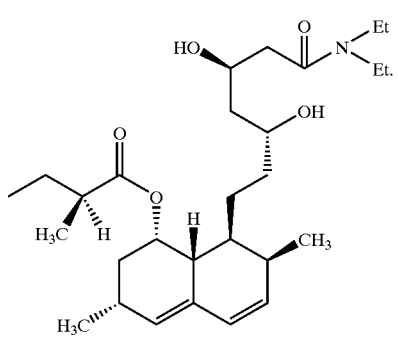

($IIb_1$)

In another embodiment, $R_1$ and $R_2$, taken together, form a 5–6 membered heterocyclic ring and the novel intermediate has the following structure:

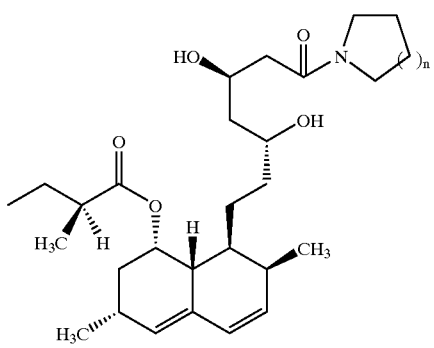

wherein n is 1 or 2.

In yet another embodiment, a novel intermediate of formula IIc is provided:

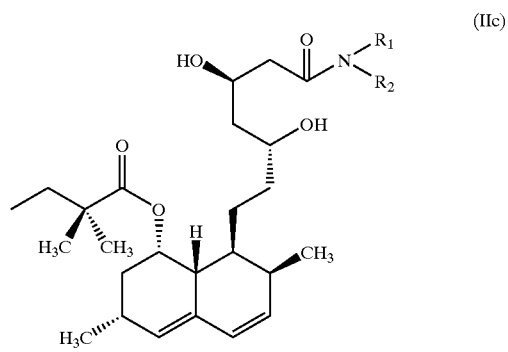

(IIc)

wherein $R_1$ and $R_2$ are each independently an alkyl, heteroalkyl, aryl or heteroaryl moiety, or $R_1$ and $R_2$, taken together, form a saturated or unsaturated heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing aryl and heteroaryl moieties may be substituted or unsubstituted.

In another embodiment, $R_1$ and $R_2$ are each ethyl and the novel intermediate has the structure $IIc_1$:

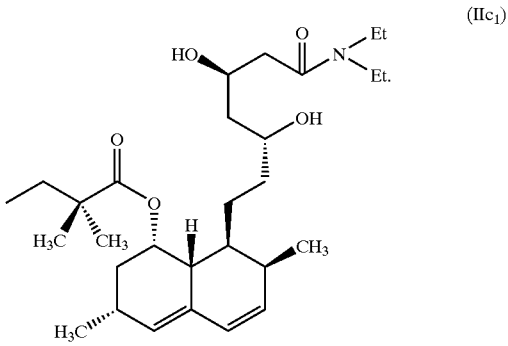

($IIc_1$)

In a further embodiment, $R_1$ and $R_2$, taken together, form a 5–6 membered heterocyclic ring and the novel intermediate has the following structure:

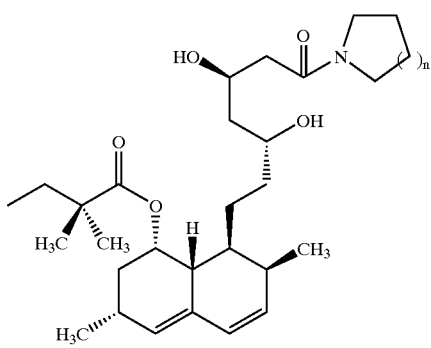

wherein n is 1 or 2.

For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity are described in "Organic Chemistry", Thomas Sorrell, University Science Books, Sausalito: 1999, the entire contents of which are incorporated herein by reference.

It will be appreciated that each of the reactions described in Schemes 1–6 above can be carried out using reagents and conditions as described for the synthesis of various types of exemplary compounds described above, or they may be modified using other available reagents or starting materials. For example, a variety of amide formation conditions, lactonization, hydrolysis and carbonyl α-alkylation reaction conditions are well-known in the art and can be utilized in the method of the invention. See, generally, March, Advanced Organic Chemistry, 5th ed., John Wiley & Sons, 2001; and "Comprehensive Organic Transformations, a guide to functional group preparations", Richard C. Larock, VCH publishers, 1999; each of which is incorporated herein by reference in its entirety.

It will be appreciated that the methods as described herein can be applied to each of the compounds as disclosed herein and equivalents thereof. Additionally, the reagents and starting materials are well known to those skilled in the art. Although the reaction schemes depicted herein describe certain exemplary compounds, it will be appreciated that the use of alternate starting materials and/or reagents used to perform the reactions will yield other analogs and/or intermediates of the invention. For example, secondary amine reagents $HNR_1R_2$ are described herein where $R_1$ and $R_2$ are each an ethyl moiety, or, taken together, form a pyrrolidine or piperidine ring; however, it will be appreciated that alternate starting materials and/or intermediates can be utilized to generate compounds where, for example, $R_1$ and $R_2$ may be independently n-propyl, isopropyl or butyl. In addition, some of the foregoing compounds can exist in various isomeric forms, e.g., stereoisomers and/or diastereomers. It is to be understood that the invention encompasses a method for preparing every possible isomer such as geometric isomer, optical isomer, stereoisomer and tautomer based on asymmetric carbon, which can occur in the structures of the compounds disclosed herein, and mixtures of such isomers, and is not limited to the specific stereochemistry shown for the compounds disclosed in the present specification. The invention additionally encompasses a method for preparing the compounds as individual isomers substantially free of other isomers and alternatively, as mixtures of various isomers, e.g., racemic mixtures of stereoisomers. It will also be appreciated that the scope of the invention is not limited to those reaction conditions disclosed in the present specification. Rather, any reaction conditions suitable to perform the synthetic transformations described herein are within the scope of the invention.

The present invention provides a highly efficient method for preparing Simvastatin and analogues thereof. The process utilizes amide intermediates that are chemically stable under the reaction conditions used in the synthetic sequence leading to Simvastatin. In contrast to certain processes of manufacturing Simvastatin known in the art, which employ primary amide intermediates, the inventive method utilizes secondary amide intermediates of general formulas IIb and IIc, lacking an amide hydrogen atom, and thus the risk of there being undesired side reactions is minimized.

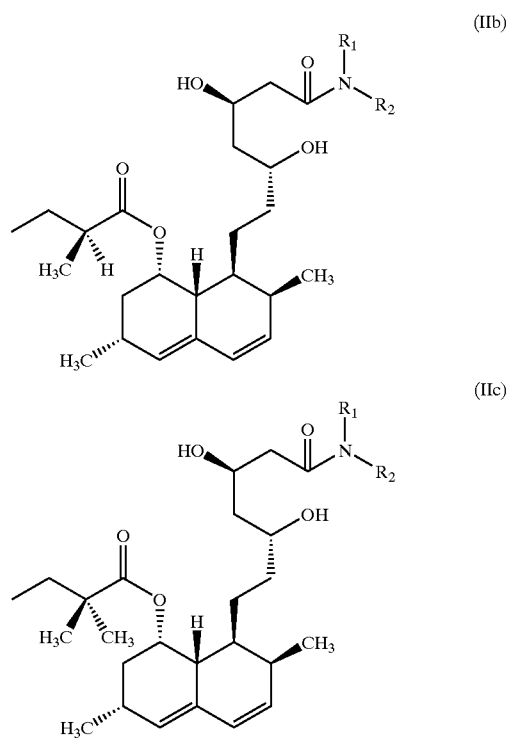

(wherein $R_1$ and $R_2$ are not hydrogen atoms)

For example, in the step involving methylation of intermediate IIb to yield intermediate IIc, potential side reactions with the base (e.g., lithium amide base) and the methylating agent (e.g., methyl halide), are avoided. It follows that the methylation reaction requires fewer equivalents of lithium amide base and thus increases the cost effectiveness of the route. In addition, the absence of the amide hydrogen atom prevents side reactions and therefore results in purer products. Consequently, downstream processing requires fewer purification steps, and thus overall yields are increased. Furthermore, the inventive process uses inexpensive raw materials and thus the costs of production are minimized.

In summary, the inventive method involves only four steps and allows the synthesis of Simvastatin and analogues thereof in a very efficient, high-yielding and cost-effective manner, and without formation of substantial amounts of undesired by-products.

Equivalents

The representative examples that follow are intended to help illustrate the invention, and are not intended to, nor should they be construed to, limit the scope of the invention. Indeed, various modifications of the invention and many further embodiments thereof, in addition to those shown and described herein, will become apparent to those skilled in the art from the full contents of this document, including the examples which follow and the references to the scientific and patent literature cited herein. It should further be appreciated that the contents of those cited references are incorporated herein by reference to help illustrate the state of the art.

The following examples contain important additional information, exemplification and guidance that can be adapted to the practice of this invention in its various embodiments and the equivalents thereof.

Exemplification

The compounds of this invention and method their preparation can be understood further by the examples that illustrate some of the processes by which these compounds are prepared. It will be appreciated, however, that these examples do not limit the invention. Variations of the invention, now known or further developed, are considered to fall within the scope of the present invention as described herein and as hereinafter claimed.

General Reaction Procedures:

Unless mentioned specifically, reaction mixtures were stirred using a magnetically driven stirrer bar. An inert atmosphere refers to either dry argon or dry nitrogen. Reactions were monitored either by thin layer chromatography, by proton nuclear magnetic resonance or by high-pressure liquid chromatography (HPLC), of a suitably worked up sample of the reaction mixture.

General Work Up Procedures:

Unless mentioned specifically, reaction mixtures were cooled to room temperature or below then quenched, when necessary, with either water or a saturated aqueous solution of ammonium chloride. Desired products were extracted by partitioning between water and a suitable water-immiscible solvent. The desired product containing extracts were washed appropriately with water followed by a saturated solution of brine. The crude products were then isolated by removal of solvent(s) by rotary evaporation under reduced pressure, at an appropriate temperature.

In general, lovastation (Ia) is reacted with a secondary amine. Preferably the secondary amine is diethylamine. In other preferred embodiments, the secondary amine is pyrrolidine or piperidine. The resulting amide is dissolved in dry tetrahydrofuran and cooled to −45° C. to −20° C. The metal amide base is prepared by adding n-BuLi to pyrrolidine and is cooled to −45° C. to −20° C. After about 1 hour, the alkyl halide, methyl iodide, is added and the contents are stirred for 30 min. Water is added to the reaction mixture and the layers obtained are separated. The organic layer is washed with brine solution and concentrated under reduced pressure to give an oily residue, which contains the intermediate methylated intermediate IIc. The crude intermediate is then hydrolyzed to give the corresponding free carboxylic acid which is converted to its ammonium salt and is cyclized to give the final product, Simvastatin.

EXAMPLE 1

Preparation of Simvastatin (II) from Lovastatin (IIa) using diethyl amine as the secondary amine Step 1: Preparation of Compound IIb$_1$

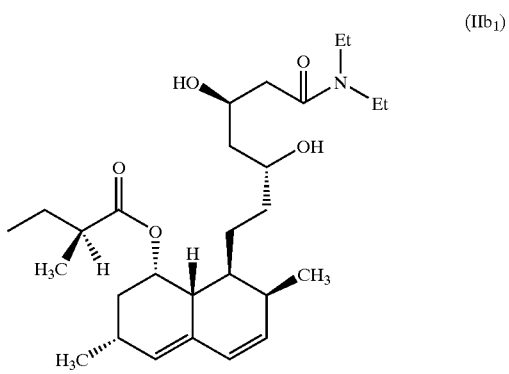

(IIb$_1$)

To a solution of Lovastatin (8.47 g) in toluene (85 mL) was added diethylamine (15 mL). The resulting mixture was heated to 90° C. and was refluxed for 36 h. The solution was cooled to 25° C. and kept at 25° C. for 4 h. The crystallized product was filtered and washed with toluene followed by hexane to afford amide intermediate IIb$_1$ in a very pure form.

Step II: Preparation of Compound IIc$_1$

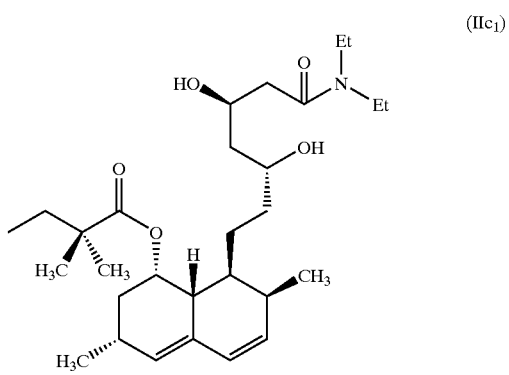

(IIc$_1$)

A solution of pyrrolidine (7.8 mL) and tetrahydrofuran (25 mL) was cooled to −30° C. A solution of n-butyl lithium (64 mL, 1.4M) was added while maintaining the temperature below −20° C. (~15 min). After the addition was complete, the mixture was aged at −25° C. for 30 minutes. A solution of amide intermediate IIb$_1$ (10 g) in THF (200 mL) was prepared and charged to the lithium pyrrolidide solution at −25° C. After the addition was complete, the mixture was agitated for 3 hours at −25° C. A methyl iodide solution was added (3.9 mL) in one portion and the agitation was continued for a further 30 min at −30° C. The mixture was quenched with water and rapidly agitated for 10 min. The phase was separated and the lower phase was re-extracted with hexane. The combined organic phase was washed with HCl (1N) and 5% bisulfite syrup, which was used for the next step without any further purification.

Step III: Preparation of the ammonium salt of Compound IIc$_1$

The syrup obtained in step II was dissolved in ethanol (20 mL) at 25° C. and a solution of NaOH (3.15 g in 20 mL of water) was charged. The resulting solution was refluxed for 3.5 hours, and was then cooled to 50° C. The ethanol solvent was distilled off under reduced pressure. The resulting mixture was diluted with water and extracted with ethyl acetate. The combined ethyl acetate extracts were back washed with 2% NaOH solution and the organic layer was discarded. The pooled aqueous layer was cooled to 10° C. and carefully acidified with 1.5N HCl to pH=4 in the presence of ethyl acetate. The aqueous layer was re-extracted with ethyl acetate and the combined organic layer was washed with water to neutral pH. 3 mL of methanol was added to the organic layer and the resulting mixture was cooled to 10° C. $NH_3$ gas was bubbled until precipitation was complete. The mixture was stirred for 30 min at 10° C. and filtered. The solid was washed with 5 mL of acetone and the product was dried to get the crude desired product.

Purification: The crude product was suspended in water and ethyl acetate was added. The mixture was cooled to 10° C. and acidified to pH=4 with 1.5N HCl. The layers were separated and the aqueous layer was re-extracted with ethyl acetate. The combined organic layer was diluted with methanol and the temperature was brought to 20–23° C. A solution of ammonium hydroxide was added slowly. The mixture was stirred for 1 hour to get complete precipitation and subsequently filtered. The precipitate was washed with ethyl acetate and dried to afford the pure desired product.

Step IV: Preparation of Simvastatin (II)

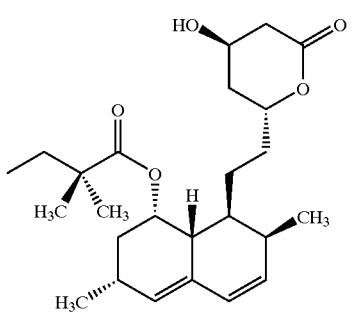

(II)

The purified ammonium salt obtained in Step III was dissolved in 150 mL of toluene and the resulting mixture was heated to 100° C. under constant sweep of nitrogen for 6 hours. The solution was cooled to 25° C. and 2.5 g of activated charcoal and 2.5 g of neutral active alumina were added. The resulting mixture was agitated for 30 min. and filtered through celite. The celite pad was washed with toluene (25 mL). The filtrate was concentrated under reduced pressure to afford a syrup. The syrup was diluted with ethyl acetate and 100 ml of petroleum ether (boiling range 60° C. to 80° C.) was added. The solution was left for aging for 30 min at 23–25° C. The precipitate obtained was filtered and the solid was washed with petroleum ether and dried at 40° C. for 2 hours to get the desired product, Simvastatin.

Purification: The crude product (4 g) was dissolved in methanol (40 mL) and 1.5 g of activated charcoal was added and stirred for 30 min. The mixture was filtered through a celite pad and the celite pad was washed with methanol. To the filtrate water was added slowly until crystallization set in. The contents were stirred for 0.5 h and water (48 mL). The contents were stirred for 1 h and cooled to 15° C. The precipitate was filtered and the solid was washed with 20% aqueous methanol (10 mL). The solid obtained was dried at 50° C. for 4 hours under vacuum to afford the pure title product.

The Simvastatin obtained was of pharmaceutical grade.

EXAMPLE 2

Preparation of Simvastatin (II) from Lovastatin using pyrrolidine as the secondary amine Step I: Preparation of Compound $IIb_2$

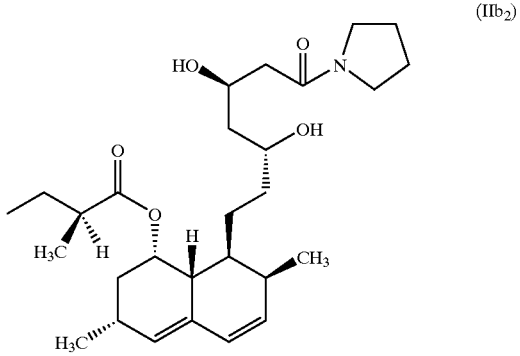

($IIb_2$)

A mixture of Lovastatin (10 g) and pyrrolidine (50 mL) was maintained at 70° C. for 6 hours. The solution was concentrated to give a syrup and chloroform was added. The extract was concentrated under reduced pressure to afford the desired amide intermediate IIb2.

Compound $IIb_2$ was converted to Simvastatin by subjecting it to steps II–IV described in Example 1.

EXAMPLE 3

Preparation of Simvastatin (II) from Lovastatin using piperidine as the secondary amine Step I: Preparation of Compound $IIb_3$

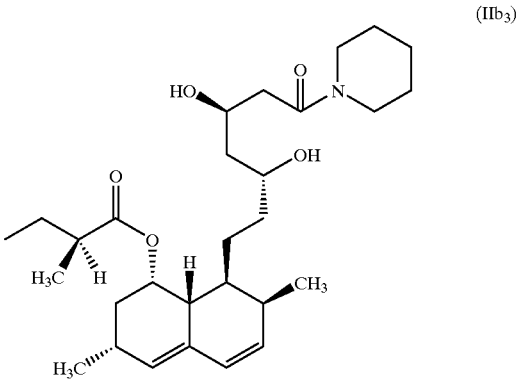

($IIb_3$)

A solution of Lovastatin (10 g) in piperidine (75 mL) was refluxed for 5 hours. Excess piperidine was removed under reduced pressure, and the residue was purified by column chromatography using 60–120 silica gel to give the pure amide intermediate $IIb_3$.

Compound $IIb_3$ was converted to Simvastatin by subjecting it to steps II–IV described in Example 1.

We claim:
1. A compound having the formula:

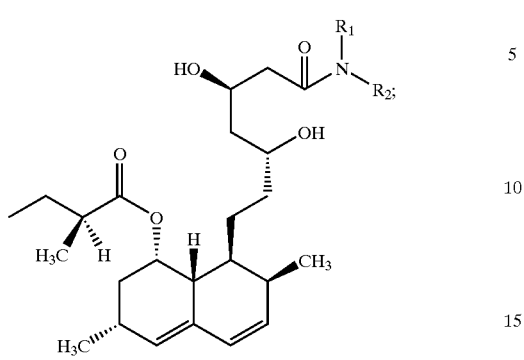

wherein $R_1$ and $R_2$ are each independently an alkyl, heteroalkyl, aryl or heteroaryl moiety, or $R_1$ and $R_2$, taken together, form a heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing heterocyclic, aryl and heteroaryl moieties may be substituted or unsubstituted.

2. The compound of claim 1 wherein $R_1$ and $R_2$ are each ethyl and the compound has the formula:

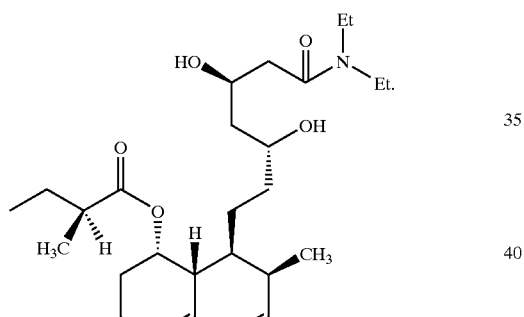

3. The compound of claim 1 wherein $R_1$ and $R_2$, taken together, form a pyrrolidinyl moiety and the compound has the formula:

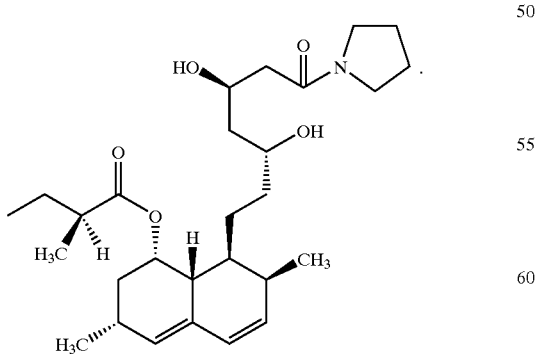

4. The compound of claim 1 wherein $R_1$ and $R_2$, taken together, form a piperidinyl moiety and the compound has the formula:

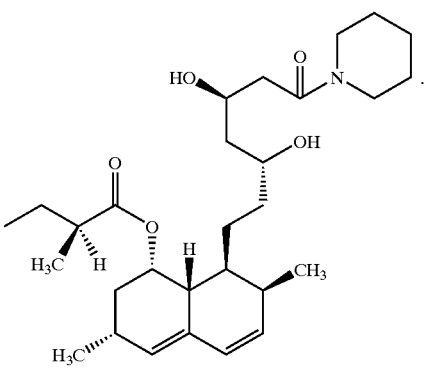

5. A compound having the formula:

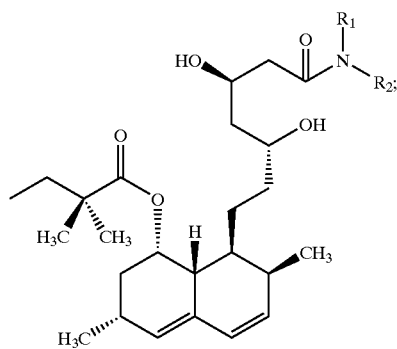

wherein $R_1$ and $R_2$ are each independently an alkyl, heteroalkyl, aryl or heteroaryl moiety, or $R_1$ and $R_2$, taken together, form a heterocyclic moiety containing 5–8 atoms; wherein each of the foregoing alkyl and heteroalkyl moieties may be linear or branched, substituted or unsubstituted, cyclic or acyclic or saturated or unsaturated, and each of the foregoing heterocyclic, aryl and heteroaryl moieties may be substituted or unsubstituted.

6. The compound of claim 5 wherein $R_1$ and $R_2$ are each ethyl and the compound has the formula:

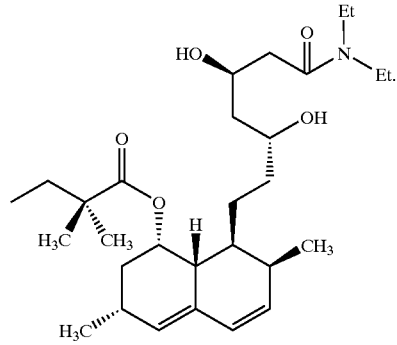

7. The compound of claim 5 wherein $R_1$ and $R_2$, taken together, form a pyrrolidinyl moiety and the formula:

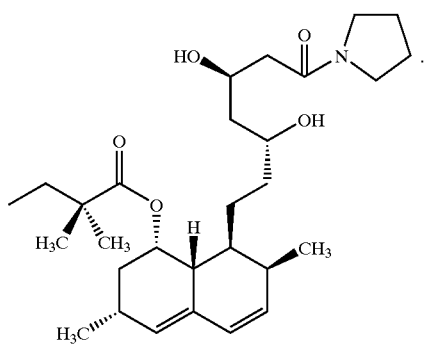
8. The compound of claim 5 wherein $R_1$ and $R_2$, taken together, form a piperidinyl moiety and the compound has the formula:
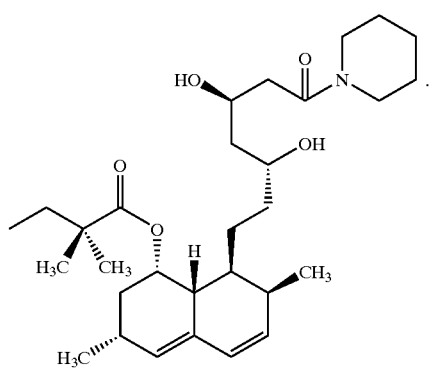
* * * * *